(12) United States Patent
Begelman

(10) Patent No.: US 6,868,309 B1
(45) Date of Patent: Mar. 15, 2005

(54) DIALYSIS MACHINE WITH SYMMETRIC MULTI-PROCESSING (SMP) CONTROL SYSTEM AND METHOD OF OPERATION

(75) Inventor: Jamie Begelman, Evanston, IL (US)

(73) Assignee: Aksys, Ltd., Lincolnshire, IL (US)

( * ) Notice: Subject to any disclaimer, the term of this patent is extended or adjusted under 35 U.S.C. 154(b) by 611 days.

(21) Appl. No.: 09/961,735

(22) Filed: Sep. 24, 2001

(51) Int. Cl.[7] .......................... G05B 21/00; G05B 11/01; G05B 15/00; G01N 33/48; G06F 19/00

(52) U.S. Cl. ...................... 700/273; 422/68.1; 422/107; 422/50; 436/43; 436/50; 436/52; 436/63; 436/66; 702/108; 702/116; 702/117; 702/118; 702/120; 700/1; 700/2; 700/5; 700/11; 700/14; 700/17; 700/18; 700/19; 700/20; 700/21; 700/23; 700/25; 700/26; 700/27; 700/266; 700/292; 700/296

(58) Field of Search .............................. 700/1, 2, 5, 11, 700/14, 17, 18, 19, 20, 21, 23, 25, 26, 27, 266, 273, 292, 296; 702/108, 116, 117, 118, 120; 422/68.1, 107, 50; 436/43, 50, 52, 63, 66

(56) References Cited

U.S. PATENT DOCUMENTS

| | | | | |
|---|---|---|---|---|
| 4,263,647 A | * | 4/1981 | Merrell et al. .................. | 700/7 |
| 4,370,983 A | | 2/1983 | Lichtenstein ................ | 128/630 |
| 4,445,174 A | * | 4/1984 | Fletcher ....................... | 711/121 |
| 4,731,731 A | * | 3/1988 | Cochran ...................... | 210/739 |
| 4,823,256 A | * | 4/1989 | Bishop et al. ................ | 714/10 |
| 5,326,476 A | | 7/1994 | Grogan et al. .............. | 219/646 |
| 5,472,614 A | | 12/1995 | Rossi .......................... | 210/646 |
| 5,487,827 A | | 1/1996 | Peterson et al. .............. | 210/87 |
| 5,591,344 A | | 1/1997 | Kenley et al. .............. | 210/636 |
| 5,618,441 A | | 4/1997 | Rosa et al. .................. | 210/739 |
| 5,620,608 A | | 4/1997 | Rosa et al. .................. | 210/739 |
| 5,759,044 A | | 6/1998 | Redmond .................... | 434/307 |
| 5,788,851 A | | 8/1998 | Kenley et al. .............. | 210/739 |
| 6,146,523 A | * | 11/2000 | Kenley et al. .............. | 210/143 |

OTHER PUBLICATIONS

"UNIX Systems for Modern Architectures: Symmetric Multiprocessing and Caching for Kernel Programmers", Curt Schimmel, Addison Wesley, 1994, pp. xxiii–xxiv, 149–173, 285–302.

\* cited by examiner

*Primary Examiner*—Jill Warden
*Assistant Examiner*—Brian Sines
(74) *Attorney, Agent, or Firm*—McDonnell Boehnen Hulbert & Berghoff LLP

(57) ABSTRACT

A method and control system computing platform for a dialysis machine that uses Symmetric Multi-Processing (SMP) architecture. The SMP architecture tightly couples multiple (e.g., 2) independent processors by sharing memory between the processors. A single shared memory is used by both processors in order to facilitate communication between the processors and reduce cost by eliminating the expense of redundant memory. In this way, the two, or in general "N" processors, increase processor throughput by allowing the execution of N processes in parallel while without requiring extra memory and without having a single point of failure in the computer. In the event of a bus failure on the circuit card, the computer is reset using distributed hardware watchdogs. The watchdog reset signal is also sent to the hardware components of the dialysis machine in order to place the system in a safe.

24 Claims, 3 Drawing Sheets

DIALYSIS MACHINE WITH SYMMETRIC MULTI-PROCESSING (SMP) CONTROL SYSTEM AND METHOD OF OPERATION

BACKGROUND OF THE INVENTION

A. Field of the Invention

This invention relates generally to the field of dialysis and machines for performing dialysis therapy. More particularly, the invention relates to a computer control system for a dialysis machine and a method of operation thereof in which a plurality of processors are provided which form a tightly coupled, symmetric multi-processing computing platform for the dialysis machine.

B. Related Art

Dialysis is a treatment for persons suffering from inadequate kidney function. A dialysis machine is an artificial kidney machine that treats the blood of a dialysis patient. Dialysis machines typically incorporate an extracorporeal blood circuit having a semipermeable dialyzer membrane. During dialysis therapy, blood from the patient is circulated through the extracorporeal circuit to the dialyzer membrane, where toxins and excess water are transported through the dialyzer membrane into a dialysate solution. The treated blood is then returned to the patient.

Dialysis machines also typically include a dialysate preparation system. This system prepares a dialysate solution by mixing concentrated chemicals (typically a mixture of sodium bicarbonate, an acid solution, and additional minerals and salts) with reverse-osmosis filtered water.

Current implementations of dialysis equipment have specific safety criteria that are required by regulatory agencies. One of these criteria is single-fault tolerance. Single-fault tolerance requires that no single point of failure of the instrumentation shall expose the patient to a hazardous condition. Historically, dialysis equipment have satisfied the criterion, in part, by designing in redundant components where indicated by risk management methodologies (e.g. hazard analysis etc.). The redundancy of components includes aspects of the computer or processor-based control system for the machine. Specifically, all dialysis machine implementations to date have incorporated a computer control system based on redundant processors which execute control and safety instructions in the form of computer code. Accordingly, redundant processors permit a remaining processor to continue operation of the dialysis machine if one of the redundant processors fails.

The failure of a processor or computer, for example, may be characterized as a Byzantine failure. The term "Byzantine" in the present document refers to a failure whose symptoms cannot be characterized. Stated differently, processor behavior during a Byzantine failure can be arbitrary and therefore potentially unsafe to the patient. As a result, two independent redundant processors may reduce the risk exposure to Byzantine failures when compared to a single processor implementation since the remaining processor may detect the malfunction and take control of the dialysis machine.

Error detection in a redundant processor architecture may therefore be provided by allowing the properly running processor to become a master and the faulty processor to become a slave. An example of a redundant processor computer control system for a dialysis machine is described in the patent of Rodney S. Kenley et al., U.S. Pat. No. 5,788,851, assigned to the assignee of the present invention, which is incorporated by reference herein. Two redundant processors, however, significantly increase an instrument's cost and complexity over a single processor design, which would be the design of choice but for the safety and redundancy requirements explained above. These increased costs include a redundant CPU board, a more complex backplane, additional software development, increased maintenance, and increased costs for servicing the machine. Furthermore, redundant processors may require separate dedicated CPU buses for each processor. As a result, a failure such as a bus lock-up condition is more likely on a system with two busses rather than one bus because a failure may occur on either bus. On the other hand, a failure on one processor may not affect the other processor if the busses are truly independent.

To reduce or eliminate the costs associated with a redundant processor controller, it is highly desirable to use a single processor design. A single processor design must, however, satisfy the same safety criterion as mentioned above, namely single-fault tolerance. Because a single processor alone has a single point of failure, i.e., the processor itself, another means must be used to detect Byzantine failures in the processor and provide for safe operation of the instrument regardless of a failure of the processor or the processor's board. A patent issued to Rosa et al. U.S. Pat. No. 5,618,441 ('441 patent), the contents of which are incorporated by reference, proposes a single microprocessor design for a dialysis machine. It is not known, however, whether a machine made in accordance with the '441 patent would meet the stringent redundancy requirements of European and domestic regulatory agencies, e.g., the Food and Drug Administration. Other prior references relating to control systems include U.S. Pat. No. 4,370,983 issued to Lichtenstein, U.S. Pat. No. 5,326,476 issued to Grogan et al., and U.S. Pat. No. 5,472,614 issued to Rossi.

SUMMARY OF THE INVENTION

This present invention solves the problems mentioned above in what is believed to be a novel manner for the dialysis industry. The solution is a control system computing platform for a dialysis machine that uses a Symmetric Multi-Processing (SMP) architecture. The SMP architecture tightly couples multiple (e.g., 2 or more) independent processors by sharing memory between the processors. In the event of a computer failure, such as a bus failure on the circuit card for example, one of the distributed hardware watchdogs may reset the computer including the processors. Therefore, it is believed that the use of the SMP type architecture represents an improvement and distinct departure from the Rosa et al. '441 patent since the SMP design uses two physical processors (in the preferred embodiment) whereas the Rosa et al. '441 patent uses a single physical processor.

Furthermore, the SMP architecture has the following advantages:

1. The SMP architecture reduces cost over a redundant architecture by eliminating expensive redundant components because they are not necessary in order to provide single-fault tolerance.
2. The SMP architecture uses a parallel multiprocessor architecture for improved performance while retaining a "single processor-programming" model thereby significantly reducing the complexity of a software application when compared to a redundant architecture.
3. The SMP architecture increases performance over a single processor controller since both processors can share the processing work-load. For example, the processors can share the work-load by evenly balancing processor loading.

An SMP controller may use a single main memory shared by both CPUs in order to facilitate communication between the processors. As a result, cost is reduced by eliminating the expense of redundant components such as redundant processors, memory and memory busses. In one embodiment, the parallel processors in an SMP controller may use a common CPU bus coupled to the shared memory, or each processor may have their own CPU bus coupled to a cache that is then linked with other processors through a separate memory bus. In contrast, redundant designs require separate redundant memories in order to maintain true redundancy resulting in additional cost. In further contrast, the two, or in general n SMP processors provide the advantage of high throughput without the added cost of redundant memory.

Additionally, the SMP controller provides increased processor throughput when compared with single processor controllers by operating on N processes in parallel without requiring redundant memory and without having a single point of failure in the controller or computer. Therefore, the SMP controller uniquely combines the advantages of increased throughput provided by redundant processor controllers while maintaining the reduced cost advantages of a single processor controller.

The SMP architecture may also connect to host adapter boards for interfacing with various dialysis machine and extracorporeal circuits. For example, these devices may include active and passive components such as control devices, sensors, motors, heaters, pumps and valve drivers. The extracorporeal circuit devices, for example, may control the flow of blood in the dialysis machine. Further, the SMP architecture may be conveniently implemented into a modular computer chassis of an SMP processing board. Maintenance costs may be reduced as a result because a single board may be replaced more economically than replacing the entire controller.

A safety consideration with SMP architecture is that the processor board itself, wherein the N tightly coupled processors may reside, may be single fault tolerant by using a watch dog timer circuit. Since there are no longer two fully independent redundant processors in the SMP architecture, such as those described in the Kenley et al. '851 patent cited above, a Byzantine failure on the processor board (a bus lockup condition for example) may be rectified with a watchdog timer resetting the processors. This prevents software execution from stopping when the CPU or I/O bus locks up.

Multiple hardware watchdogs distributed (with respect to the system boards) in an SMP architecture may remedy a controller failure in a novel and much less expensive manner than in a redundant processor architecture. In one embodiment, the CPUs may periodically reset the watchdog timers before the timers "time-out". Accordingly, the periodic receipt of the watchdog reset signals from the CPUs may indicate that the CPUs are operating properly. On the other hand, if the CPUs fail to reset the watchdog timers, then the watchdog timers may time-out by counting down to zero or alternatively to a predetermined number. For example, the CPU may fail to reset the watchdog timer due to a Byzantine failure such as a CPU or bus lock up condition. Accordingly, in the event of a failure, the watchdog timer may send a reset signal to reset the CPUs in order to correct the failure. Therefore, should the watchdog timer circuit fail to receive the periodic reset signals within the expected time interval(s), the CPUs may be reset. Since the watchdogs are physically independent of the processor board, the watchdogs are unaffected by Byzantine failures on it. Additionally, because there are multiple watchdogs in the system, the watchdog circuitry itself is single-fault tolerant.

The watchdog timer circuits may respond to a controller failure by delivering a control signal to these various dialysis machine and extracorporeal circuits. As a result, the watchdog reset signal may also be sent to the various hardware components such as the extracorporeal circuits of the dialysis machine in order to place the system in a safe mode. Accordingly, the control signal may effectively de-energize the extracorporeal control and hydraulics devices to cause the dialysis machine to assume the safe patient mode. The safe mode may also shut off the flow of blood to the patient from the dialysis machine in order to prevent any damaged or unsafe blood from flowing to the patient. For example, the flow of blood to the patient may be stopped by disabling the blood pump and closing a clamp in the venous line. A failure of the controller therefore effectively results in the dialysis machine entering the safe patient mode.

In accordance with the preferred embodiment of the present invention, an improved control system for a dialysis machine is described. The improved control system is single fault tolerant by utilizing multiple watchdog circuits in an SMP architecture. The foregoing and other features and advantages of preferred embodiments of the present invention will be more readily apparent from the following detailed description, which proceeds with references to the accompanying drawings.

BRIEF DESCRIPTION OF THE DRAWINGS

Presently preferred forms of the invention are depicted in the appended drawing figures, where like reference numerals refer to like elements in the various views and wherein.

DETAILED DESCRIPTION OF THE PREFERRED EMBODIMENT

Figure 1:
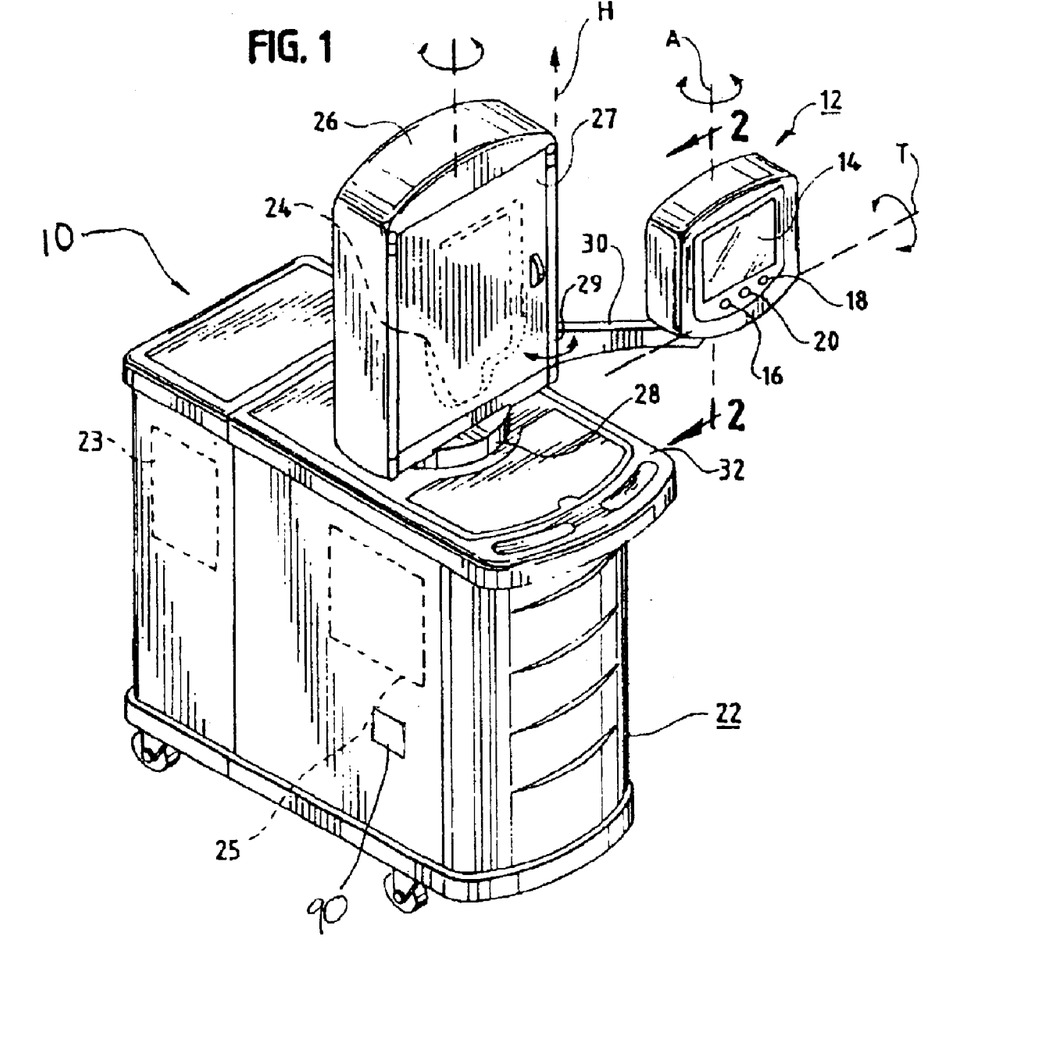
FIG. 1 is a perspective view of a dialysis machine.

FIG. 1 illustrates an exemplary dialysis machine 10 shown in a perspective view. As explained in the previously incorporated U.S. Pat. No. 5,788,851 patent, the dialysis machine 10 includes a patient or user interface module 12 containing a touch screen display 14 and a set of hard keys 16, 18, 20. The user interface module 12 is connected to an SMP control system 90 for controlling the functions of the dialysis machine as shown in FIG. 2 in more detail.

The dialysis machine 10 shown in FIG. 1 has an integral water treatment 23 and dialysate preparation module 25 contained within a lower cabinet 22. An extracorporeal blood circulation circuit is housed within an upper cabinet 32. The integral water treatment 23 and dialysate preparation modules 25 are described in detail in U.S. Pat. No. 5,591,344 to Kenley et al. and assigned to Aksys, Ltd., the assignee of the present invention, and in PCT application publication no. WO 96/25214. These references describe a preferred dialysis machine suitable for use in the home environment. The Kenley et al. U.S. Pat. No. 5,591,344 and published PCT application no. WO 96/25214 are both fully incorporated by reference herein. Additionally, the manner in which the dialysate solutions are prepared and circulated through the dialysate circuit may be as described in the above-referenced Kenley et al. U.S. Pat. No. 5,591,344.

Blood is removed from the patient and introduced into an arterial line, and pumped by a blood pump to the blood chamber of a dialyzer 10 in the extracorporeal circuit within cabinet 32. Blood-borne toxins and excess water are removed from the blood through the membrane of the dialyzer, and the blood is returned to the patient via a venous line. As previously stated, the details of the dialysate preparation module 25, water treatment module 23, and extracorporeal blood circuit are discussed in Kenley et al. U.S. Pat. No. 5,591,344. Therefore, a detailed discussion of these aspects of the instrument is omitted.

Figure 2:
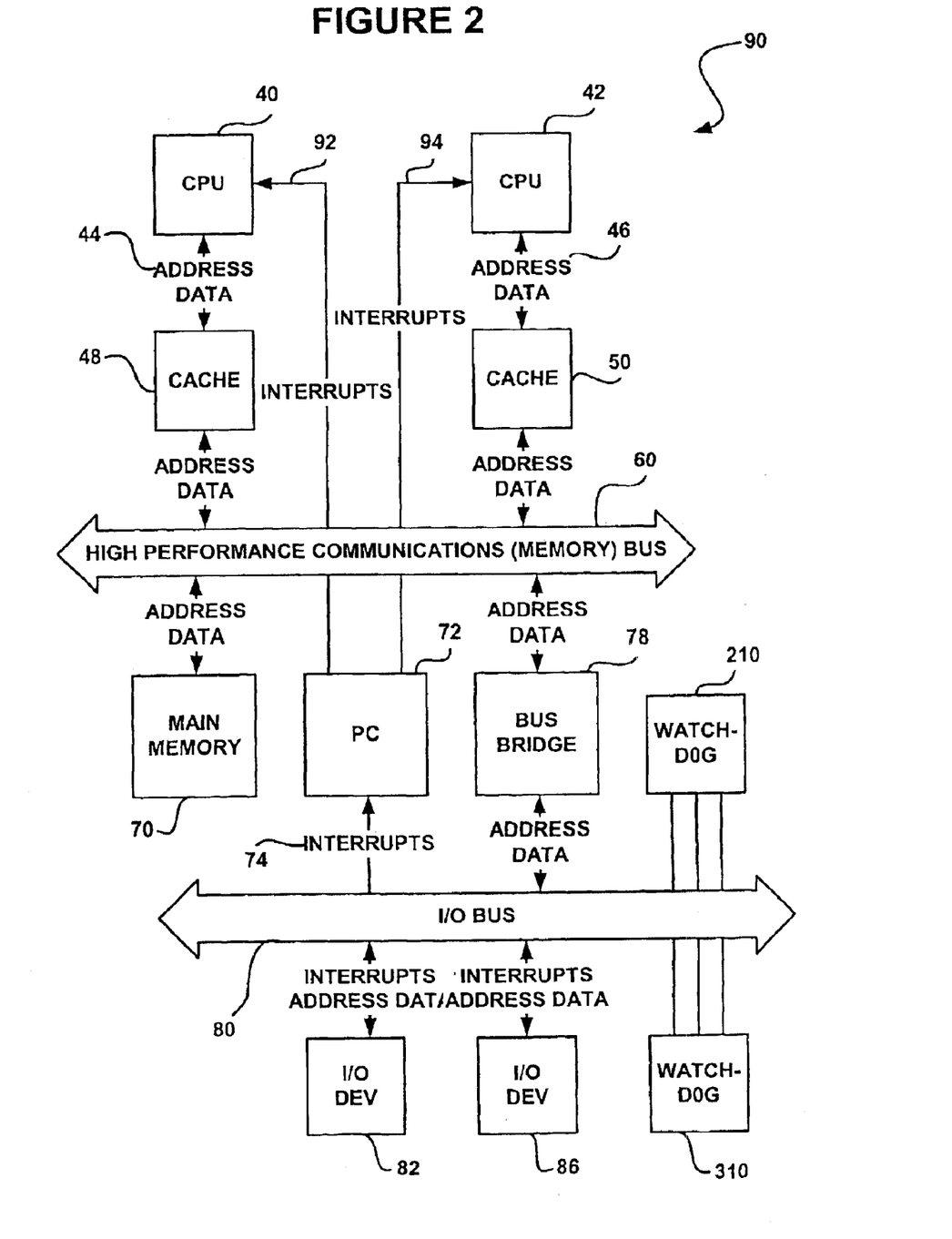
FIG. 2 illustrates a block diagram for one embodiment of the SMP architecture for the controller in the dialysis machine of FIG. 1.

Referring to FIG. 2, a preferred embodiment of an SMP control system 90 is shown. It will be readily apparent that the SMP control system 90 of the present invention could be used in many types of dialysis machines other than the one shown in FIG. 1. For example, the SMP control system 90 may be used in the dialysis machines described in the patents to Grogan et al. U.S. Pat. No. 5,326,476 and Rosa et al. U.S. Pat. No. 5,618,441, the contents of which are incorporated by reference. Further, the SMP control system 90 of the present invention could also be used in other machines currently marketed by Gambro, Cobe, Baxter Healthcare, Althin Medical, and others.

SMP Architecture

FIG. 2 illustrates a presently preferred architecture for a SMP control system 90. The control system 90 generally includes multiple tightly coupled central processing units (CPUs) 40, 42 that share a common main memory 70. Main memory 70 may be RAM (Random Access Memory), PROM (Programmable Read Only Memory), hard drive, ASIC (Application Specific Integrated Circuit) or any other suitable storage device for storing program code and data. Although two CPUs 40 and 42 are shown, the SMP control system 90 may be extended to more CPUs such as 3, or more CPU's. The current version of the Windows NT, XP, ME, or 2000 operating system, for example, may support up to 32 processors. Consequently, as the performance and capabilities of future processors and operating systems increase, the SMP control system may be able to support more CPUs in the future. Generally, the processors in an SMP system are identical or are from the same type of processor family. Nevertheless, it may be possible to use different models from the same processor family or even processors from different vendors. For example, processors from Intel, Motorola, Texas Instruments, AMD or any vendor may be used. Processors that support SMP are preferably used. Alternatively, extra circuitry may be added external to the processor in order to support SMP functions.

Figure 3:
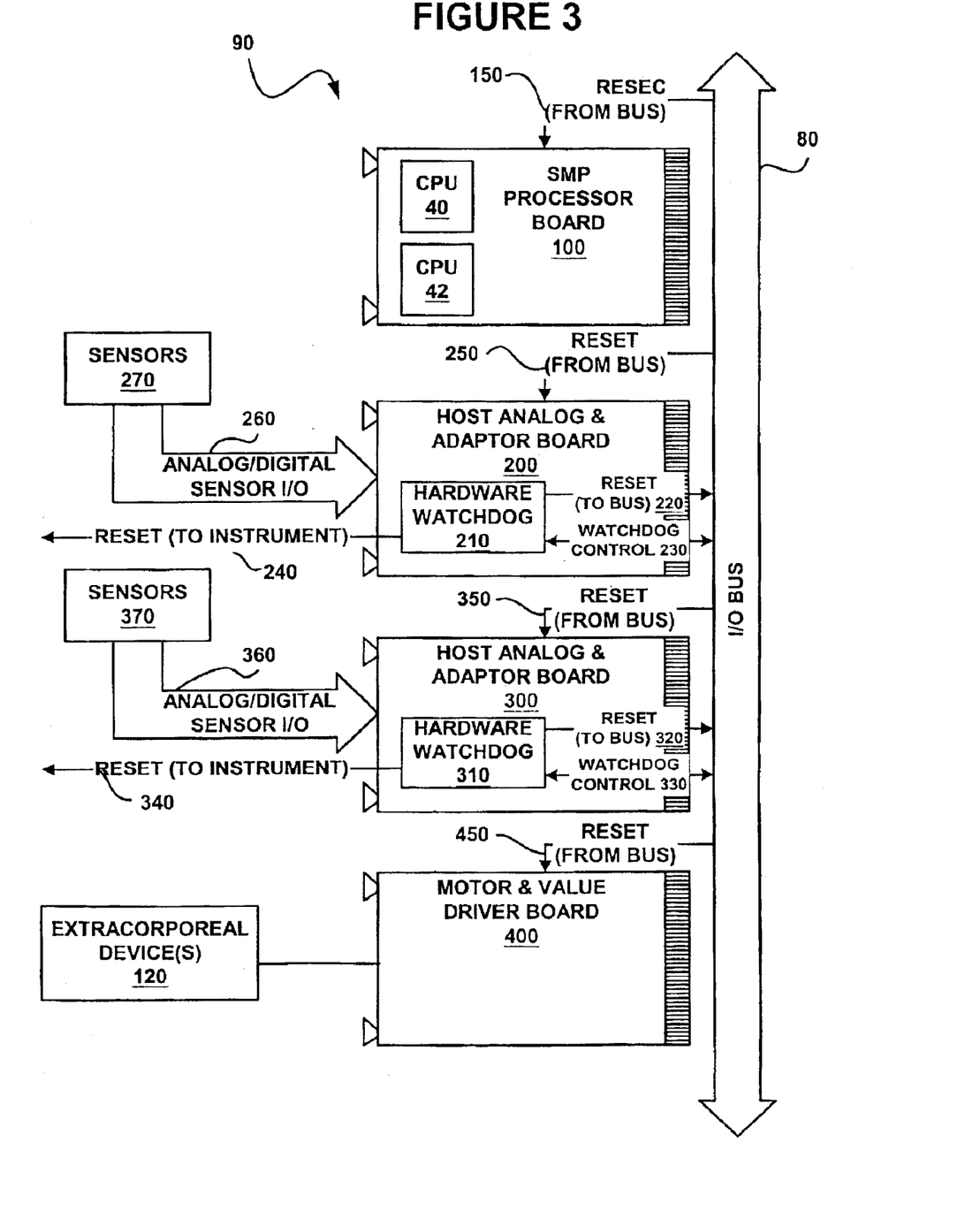
FIG. 3 illustrates one embodiment of distributing the SMP architecture into modular circuit cards.

As shown in FIG. 2, the SMP control system 90 may use a high performance memory bus 60 for high speed communications between the processors 40, 42 and the main memory 70. Additionally, exemplary I/O devices 82, 86 may generally communicate on an I/O bus 80 rather than directly over the high performance communications (memory) bus 60. Exemplary I/O devices 82 and 86 may for example be, extracorporeal devices such as valves, pumps, heaters, lights and motors 120 as shown in FIG. 3. One advantage of using the separate communications (memory) bus 60 and the separate I/O bus 80 is that CPUs 40, 42 may operate at a higher clock speed than the clock on the I/O bus 80 as is often the case. Accordingly, in order to transfer data between these busses, the I/O bus 80 may be connected to the high performance bus 60 through a bus bridge 78. The bus bridge 78, for example, may emulate a direct connection by performing any data formatting and data rate adaptation between the two buses. For example, the I/O bus 80 may interconnect exemplary I/O devices 82, 86 to main memory 70 or CPUs 40, 42 using bus bridge 78. Alternatively, bus bridge 78 may de-couple the I/O bus 80 from the high performance bus 60 when data transfer between these two busses is not required.

In one embodiment, CPU 40 may be linked to a cache 48 via the local CPU address/data bus 44. Analogously, the second processor, CPU 42, may be linked to a cache 50 via a local CPU address/data bus 46. Caches 48 and 50 may then be linked to the high performance communications (memory) bus 60 to facilitate communication between the processors. Caches 48, 50 can enhance processor 40, 42 throughput by taking advantage of the highly repetitive and predictable computations executed in an application. For example, the most recently executed instructions, and therefore the most likely next executed instructions, may be stored in caches 48, 50 in order to allow CPUs 40, 42 fast access to the instructions. Consequently, caches 48, 50 eliminate the need to access a slower device such as a hard drive or a main memory in order to retrieve recently executed instructions.

This architecture shown for example in FIG. 2 is a tightly coupled, shared memory, symmetric multi-processing (or simply symmetric multi-processing—SMP) hardware architecture using two or more symmetric physical processors, 40 and 42 in such a manner that they appear to act as a single logical processor to a software application. The architecture is characterized by the following properties.

(1) Tight coupling of processors 40, 42 and memory 70: The tight coupling of processors 40 and 42 means that all elements such as processors 40, 42, and memory 70 can communicate directly with each other (typically through the common high performance communications bus 60 although various types of switching networks may also be used). The high performance communications (memory) bus 60 may also interconnect with main memory 70. Additionally, the high performance communications (memory) bus 60 may access an I/O bus 80 via a bus bridge 78.

(2) There may be a single main memory 70 that is global to all processors and shared by all processors 40 and 42. In one embodiment, there preferably are not processor-private random access memories in the system other than from processor caches 48, 50. In another embodiment, memory 70 may be made of separate memory components such as memory integrated circuits while appearing as a single main memory. For example, multiple memory or virtual memory components 70 may provide access to CPUs 40, 42 or caches 48, 50.

(3) Access to the single main memory 70 is symmetric and fair. In other words, any memory operation means the same thing whether performed by any processor (i.e. CPU 40, 42) or any I/O device 82, 86.

The SMP control system 90 may link to the interface module 12 shown in FIG. 1 via the I/O bus 80, PIC (Programmable Interrupt Controller) 72, and I/O devices 82, 86 for example. The PIC 72 may connect to all external interrupt sources to arbitrate interrupt requests 92, 94 for access to the CPUs 40, 42. Additionally, I/O devices 82, 86 may interface with the CPUs 40, 42, PIC 72, and the I/O bus 80 to provide supervisory control. As a result, the interface module 12, shown in FIG. 1 in conjunction with the SMP control system 90 shown in FIG. 2, may exercise supervisory control over the operation of the dialysis machine 10 and further display the current status of the dialysis machine 10 and treatment options. For example, the interface module 12 may prompt the user to input commands and information. Additionally, the user interface and method of operation is applicable to other types of medical instruments. For further details of the user interface, see U.S. Pat. No. 5,788,851 cited earlier.

Hardware Watchdog Circuits 210, 310 (Fault Recovery)

Hardware watchdog circuits 210 & 310 are programmable hardware timers that have the capability of electrically resetting the computing platform should they time out. Watchdog timers 210 and 310 may interface with the CPUs 40, 42, a dedicated reset controller (not shown), the I/O bus 80 and the local CPU bus 60. Watchdog timers 210 & 310 as shown in FIG. 2 may be reset by CPUs 40 & 42 in order to start the watchdog timers 210 & 310 onto a countdown. The watchdog timers 210 & 310 then count down towards zero from a predetermined amount of time. A hardware reset of watchdog timers 210 & 310 normally occurs before the timer counts down to zero if there is no failure such as a bus (i.e., CPU bus 60 or I/O bus 80) lock-up condition preventing the CPUs 40 & 42 from resetting watchdog timers 210 & 310. Other types of computer failures may include an interrupt failure, a memory failure, a disk failure, clock failure, a watchdog failure, a peripheral failure, a software failure and a CPU failure and any bus failure related to these and other components. Analogously, any failure may be deemed to be the result of any cause preventing CPUs 40 and 42 from resetting the watchdog timers 210 and 310.

During normal operation, CPUs 40 and 42 periodically reset the watchdog timers 210 and 310 before the timers time-out. The periodic receipt of the signals by the watchdog timers 210 and 310 from the CPUs 40 and 42 indicates that the CPUs 40 and 42 are operating properly. As a result, if the CPUs 40 & 42 fail to receive the periodic signals within the expected time interval(s), then the watchdog timers 210 and 310 are not reset and the watchdog timer times-out. The watchdog timers 210 and 310 may time-out, for example, due to a CPU or bus lock up condition as previously stated. As a consequence of not being reset, the watchdog timer 210, 310 may send a reset signal to reset CPUs 40 and 42 to force a system reboot. In another embodiment, the watchdog timers 210 & 310 may be reset at different intervals and have different count-down time periods in order to prevent double resets for example. Additionally, a reset controller or similar mechanism in either hardware or software would avoid a double reset.

The watchdogs 210 and 310 may be physically independent of the processor board 100. As a result of being independent, watchdogs 210 and 310 are unaffected by Byzantine failures. Because there are multiple watchdogs in the system, the watchdog circuitry itself is single-fault tolerant. If one watchdog fails, then the other watchdog may reset the controller 90 in the event of a failure. In one exemplary embodiment as shown in FIG. 3, multiple hardware watchdogs 210 and 310 are located on separate modular circuit boards 200 and 300 respectively. If the processor board suffers a Byzantine failure, the watchdogs 210 and 310 can still reset the system because they are physically independent of CPUs 40 and 42. If, for example, watchdog 210 fails during operation then other watchdog 310 protects against processor failures. Analogously, if watchdog 310 fails during operation then other watchdog 210 protects against processor failures. Consequently, since the watchdogs provide a way to recover from a bus or processor failure, the present invention is single-fault tolerant. Additionally, the watchdog timer may, for example, be based on the Intel MCS 51/151/251 family of microcontrollers.

Safe Mode

In a dialysis instrument, the watchdog reset signals such as 240 and 340 shown in FIG. 3 may also be sent to other hardware components of the dialysis machine 10 in order to control these components, or to place all electromechanical subsystems into a safe state. For example, the watchdog timer circuits 210 and 310 may respond to a controller 90 failure by delivering a control signal 240 and 340 to the extracorporeal circuit devices (e.g. blood pump and venous line clamp) and selected hydraulics control devices contained within the valves, motors and pumps 120 as shown in FIG. 3. Consequently, the hardware watchdogs 210, 310 may shut off the blood pump, motors, heaters and bypass values 120 in the dialyzer to assume the safe patient mode. As a result, the safe mode may shut the flow of blood to the patient from the dialysis machine 10 in order to prevent any potentially unsafe blood from flowing to the patient. The safe mode may involve closing the arterial and venous clamps, stopping the arterial blood pump, the venous blood pump, and bypassing the flow of dialysate around the dialyzer by changing the state of the bypass valves. Therefore, a reset signal to the CPUs 40 and 42 effectively achieves the safe patient mode.

In the event that the CPUs 40, 42 are reset in the absence of a controller failure, then there is no risk to the patient in any event because the dialysis machine is placed into a safe state. For example, if a failure on the watchdog timers 210, 310 causes the CPUs 40, 42 to reset, then the controller puts the dialysis machine 10 into a safe mode, so there is no risk of injury to the patient. After the controller is placed into a safe state, then the controller may perform a self-check, resolve any bus contention and resume normal dialysis operation. The self-check may include determining if all dialysis programming information is correct and verifying the programming information with the patient or user before resuming dialysis.

Bus Collision Avoidance and Detection

In an exemplary embodiment, access to the high performance (memory) bus 60 between CPUs 40 and 42 and caches 48 and 50 may be arbitrated by one of several ways. For example, the operating system may allocate bus access time to each processor 40 & 42 based on the allocation and timing of executable instructions to each processor. Since the operating system determines how the executable instructions are distributed between the processors 40 & 42, then the operating system may also determine the most effective distribution of bus access to each processor based on instruction length and complexity.

Alternatively, or in combination with the operating system, each processor 40 and 42 may make a bus access request to, for example, a master bus controller in order to control access to the high performance bus 60. The master bus controller may then resolve multiple requests or any conflicting requests and integrate bus access requests with normal operating system bus access requests.

Yet another technique for detecting and avoiding bus collisions, or in combination with the above techniques, is to allow each processor 40 or 42 access to the high performance bus 60 based on either processor 40 or 42 first detecting activity on the bus 60 before driving the bus 60. If no activity is sensed on the high performance bus 60, then the processor 40 or 42 sensing no activity may take control of the bus 60. If activity is detected on the high performance bus 60, then, the processor 40 or 42 sensing the activity may wait a pre-determined amount of time to again detect bus activity, or until the bus is released. Accordingly, once a processor releases the high performance bus 60, then another processor 40 or 42 may take control of the bus after detecting no activity. If, however, both processors try to drive the bus 60, then a protocol allowing a response or acknowledgement to a processor driving the bus will inform the processor if the message or command was received. For example, the CPU driving the bus may not receive a response to the message or command because, for example both CPUs attempted to drive the bus causing a collision. Accordingly, both CPUs may release the bus and again attempt to drive the bus after performing the collision avoidance techniques above.

An alternative technique for detecting a collision on the bus 60 is to employ a dedicated collision detection circuit for informing the processors that the bus 60 is in use by one or more components. Once the component such as processor 40 or 42 receives a collision signal from the collision detector, the component may interrupt driving the bus 60 and release the bus for an amount of time statistically pre-determined to minimize collisions. Additionally, any combination of the above mentioned or well-known bus resolution techniques may be utilized.

Alternatively, a processor error may be detected during normal operation where the redundant processors may compare each other's computational results while executing command instructions. For example, if the results between the processors differ, then the processors may perform a self-test. Accordingly, if one processor fails the self test, then the remaining properly functioning processor may take control of the dialysis machine and reset the failed processor. Alternatively, an arbitrator circuit may detect if there is a difference in the computational result of each processor. If there is a difference, then the arbitrator may then determine which processor is in error and assign control of the dialysis machine to the remaining, properly functioning processor.

Element-to-memory communications arbitration may be performed on an equal time basis between elements. If any processor (i.e. CPU 40, 42) reads physical memory address n, for example, then any other device such as an I/O device 82, 86 may also read physical memory address n so that the same physical datum may be read twice. If, for example, processors 40, 42 and/or I/O devices 82, 86 access the main memory 70 simultaneously, then their access may be arbitrated so that each computing element (processor 40, 42 or I/O device 82, 86) receives an equal amount of element-to-memory communications bandwidth. Furthermore, the arbitration process may be transparent to the computing elements such as processors 40, 42. For further details, see *UNIX Systems For Modern Architectures: Symmetric Multiprocessing And Caching For Kernel Programmers*. Addison Wesley 1994, e.g. at section 8.2, page 152.

Modular Architecture

FIG. 3 illustrates the SMP control system 90 shown in FIG. 2 distributed among several modular circuit cards according to one embodiment of the present invention. As shown in FIG. 3, an SMP processor board 100 may be interconnected to an I/O bus 80 back plane. Exemplary CPUs 40 and 42 may be mounted on the SMP processor board 100. Additionally, caches 48, 50, and PIC 72, (shown in FIG. 2) may be connected to CPUs 40, 42 via CPU bus 60 and may also be part of the SMP processor board 100. Further yet, main memory 70 and bus bridge 78 (also shown in FIG. 2) may be mounted on the SMP processor board 100. A reset line 150 may link the SMP processor board 100 with the I/O bus 80 back plane in order to provide the reset signal to CPUs 40 and 42 from the watchdog timers 210 and 310. The reset line 150 may be coupled directly to CPUs 40 and 42, or may be coupled through another device such as a reset controller (not shown) or PIC 72.

A host analog and adapter board 200, 300 may link to the I/O bus 80 via address, data, and other signals or buses. As shown in FIGS. 2 and 3, a hardware watchdog 210, 310 may be mounted on host analog and adapter boards 200, 300 to interface with I/O bus 80 via a reset line 220, 320 and a watchdog control line 230, 330. Additionally, hardware watchdogs 210, 310 may interface to sensors 270, 370 as well as other patient critical components of the dialysis machine 10 (shown in FIG. 1) such as pumps, valves, heaters, motors, and other active components 120 via reset 240, 340, 230, 330, and I/O bus 260, 360. A reset signal on reset line 250, 350 may cause these components to switch to a safe mode of operation. For example, in the case of a pump, the pump is stopped, and in the case of a valve, the valve may open or close. Additionally, reset lines 220, 320, 330, and 250, 350 may connect to processors 40 and 42 or alternatively to a reset controller on the SMP processor board 100. In another alternative, reset lines 220, 320, 230, 330, 250, 350 may connect to PIC 72 or an interrupt I/O device such as I/O device 82 or 86. Reset lines 250, 350 may be used to reset the devices on the host analog & adapter board 200 300 such as hardware watchdogs 210, 310.

The signals from analog or digital sensors 270, 370 may interface to the analog/digital sensor bus 260, 360 and then to I/O bus 80 via the host analog & adapter boards 200, 300. Analog or digital sensors 270, 370 may for example be conductivity sensors, pressure sensors, temperature sensors, or any other appropriate type of sensors or transducers. Reset lines 250, 350 may link the host analog and adapter board 200, 300 with I/O bus 80.

Finally, FIG. 3 illustrates a dialysis motor, heater and valve driver board 400 interfacing to I/O bus 80, reset line 450 and extracorporeal device(s) 120. Reset line 450 may reset the extracorporeal devices 120 (valve, heater, motor and pumps etc.) coupled to the motor and valve driver board 400. Analogously, reset lines 250, 350 may therefore be used to reset the devices on the host analog & adapter boards 200, 300 as well as. Furthermore, although the exemplary SMP computer 90 is shown distributed among four circuit boards, the SMP computer may be divided among greater or fewer than four circuit boards and may further depend on the physical lay-out of the dialysis machine 10.

SMP Operating System

An SMP operating system may coordinate access to the high performance bus 60 via controlling access by the processors 40, 42, memory 70, and the bus bridge 78. The SMP operating system may allow the SMP controller 90 to generally execute one or more processes by simultaneously executing or processing N instructions in parallel where N is the number of processors. A process may be a software application, a module from a software application, a single instruction, an operating system command or any group of machine instructions, or other type or group of instruction. In one embodiment, several processes may be executed on separate processors, however, in another embodiment one process may also execute on more than one processor simultaneously by distributing instructions from a process amongst the processors.

In one embodiment, the SMP operating system may allow different processes to execute in parallel on different processors. Accordingly, n SMP processors may each execute different instructions from n different processes in order to execute the n processes simultaneously. In this embodiment, the SMP operating system executes different processes simultaneously and may be used where the operation of each process may be time critical. For example, one processor may execute a process for a safety function and another processor may execute a process for a control function. The net effect for an SMP system with n processors is that up to n times as much work can be performed per unit of time when compared to a single or redundant processor system. If, however, a first process on one processor is dependent on a second process on another processor, then the first process may have to wait for the second process to finish.

In another embodiment, processes may be executed sequentially. In this case, multiple instructions from the same process may be distributed for execution among the n processors thereby reducing the execution time of any single process. In other words, at any instant in time, n different instructions of any single processes may be executing on n processors. In contrast, a single-processor operating system only executes a single instruction or process at any instant in time. As a result, the single processor operating system merely creates the illusion of many virtual processes executing concurrently by rapidly switching execution between the different processes according to the single processor operating system's schedule. Therefore, in contrast to both the single processor and redundant processor systems, the SMP operating system and computer may execute a process more quickly because the SMP operating system may execute different instructions in a true parallel processing computer while using a single main memory.

In yet another embodiment, the SMP operating system may switch execution among processes using distributed instruction-scheduling policies. Additionally, an SMP operating system does not necessarily favor any of the n parallel processors. For example, the operating system may assign the first available processor to be used for executing the next instruction or process. If, however, processes are executed in sequence, then neither process is favored over another because the processes are executed independently.

The SMP architecture and operating system allows the presence of multiple physical processors to appear transparent to an application. When an application executes on an SMP operating system, the application is not necessarily aware that processes, commands, and instructions may be constantly scheduled on different physical processors by the SMP operating system. The application preferably is not necessarily required to track or perform symmetric access to shared memory, rather, this function is performed by the operating system. Consequently, application software can simply be written as if it is to execute on a single "virtual" processor.

The single-processor programming model used in the SMP controller 90 is simpler than a programming model with redundant dedicated host and safety computing platforms. For example, the redundant computer architecture has a separate redundant memory for each controller whereas the SMP controller may function with a single memory. The CPUs in the SMP architecture do not require redundant I/O busses whereas a redundant computer uses redundant I/O buses to interface with extra corporeal devices. The redundant dual processor type architecture, however, is visible to application software and increases the complexity of the application software. For example, a significant portion of the redundant programming model is devoted to a synchronizing processes for distributing applications and processes on both processors as required in the '851 patent. In contrast, synchronization in the SMP operating system used in the SMP controller becomes trivial because the SMP operating system uses the single-processor programming model.

Further, independent and redundant processors are different from an SMP system in that the redundant processors perform independent redundant tasks rather than load share as in the SMP architecture. Although the single-processor programming model may utilize two physical SMP processors sharing the work load, the SMP operating system and not the application manages processes between the processors. Unlike the redundant and single processor architectures, in the SMP architecture, the application appears to simply work as a single virtual processor. Therefore, the redundant physical processor model of the '851 patent is undesirable due to the increased complexity and the resulting increased hardware and software costs. Similarly, unlike the SMP operating system, the single processor model is undesirable because the application is required to manage different processes. Additionally, the single processor controller will have less throughput than an SMP type computer assuming equivalent individual computers because the SMP architecture permits different processes to be executed simultaneously on different processors.

Nevertheless, a non-SMP operating system can be used on an SMP-enabled controller to achieve some degree of computing parallelism. For example, in a two processor SMP controller, a non-SMP O/S might only run on one process, for example, on the first processor and multitask processes on that processor. The non-SMP operating system could then treat the second processor as a slave by executing different processes one at a time on the second processor such that the process must run to completion before starting the next application. In this context, there are two processes executing in parallel at any given instant. For example, one process may be running in a multitask mode on the first processor, while another process is executing on the second processor. A similar type of scheme is described as a "master-slave" kernel in UNIX Systems For Modern Architectures; Shimmel, Curt; Addison-Wesley, 1st edition (May 26, 1994); ISBN 0-201-63338-8. In this scheme, the processors are not treated symmetrically by the operating system because the second processor is scheduled differently from the first processor.

In contrast, the SMP enabled operating system truly treats all computing resources symmetrically. The SMP operating system and its subsystems can be scheduled and executed on any processor in the system in exactly the same manner as the operating system schedules and executes processes.

Other implementations for the features described may be incorporated into a generalized SMP type of architecture. For example, the number of CPUs in the SMP can be generalized as "N" CPUs including 2, 3, 4, 32 or more CPUs as previously stated. Similarly, the synchronization and distribution of the machine instructions may be performed by the operating system, or alternatively by dedicated hardware such as a dedicated programmable logic array, or a CPU. Additionally, the synchronization and distribution of the machine instructions may be performed by a software routine in conjunction with or without the operating system, a module to the operating system, or on another processor.

Preferred and alternative embodiments of the present invention have been illustrated and described. It will be understood, however, that changes and modifications may be made to the invention without deviating from its true spirit and scope, as defined by the following claims.

I claim:

1. Medical apparatus comprising:

a dialysis machine having a plurality of active and passive mechanical components, including one or more pumps and valves, and a control system for operating said mechanical components of said dialysis machine, the control system comprising:

a plurality of processors and a main memory shared by said plurality of processors forming a symmetrical, multi-processing computing platform; and a plurality of distributed hardware watchdog timers coupled to said plurality of processors such that said plurality of hardware watchdog timers reset at least one of said plurality of processors in the event of a failure of said at least one of said processors, thereby providing improved fault tolerance of said control system for said dialysis machine and thereby insuring proper and safe operation of said mechanical components of dialysis machine.

2. A control system for a dialysis machine, the control system comprising:

a plurality of processors and a main memory shared by said plurality of processors forming a symmetrical, multi-processing computing platform; and a plurality of distributed hardware watchdog timers coupled to said plurality of processors such that said plurality of hardware watchdog timers reset at least one of said plurality of processors in the event of a failure of said at least one of said processors, wherein if said plurality of processors fails to reset said plurality of distributed watchdog timers and at least one of said plurality of distributed watchdog timers timeout, then at least one of the plurality of hardware watchdog timers sends a signal to one or more hardware components of said dialysis machine in order to place said dialysis machine into a safe mode.

3. The control system for said dialysis machine of claim 2 wherein said failure of said plurality of processors to reset said plurality of watchdog timers is chosen from the group consisting of: memory bus contention, I/O bus contention, processor failure, cache failure; watchdog timer failure, software failure and local CPU bus contention.

4. The control system for said dialysis machine of claim 2, further comprising:

a memory bus coupled to said plurality of processors and said main memory wherein said plurality of processors share said main memory.

5. The control system for said dialysis machine of claim 4, further comprising:

a plurality of caches coupled to said memory bus and coupled to a corresponding plurality of processors; and a plurality of local CPU buses interfacing each of said plurality of processors to each of said plurality of caches.

6. The control system of claim 5, wherein said plurality of processors further comprises:

a first processor and a second processor, said first and second processors and said main memory forming a tightly-coupled, symmetrical, multi-processing computing platform; and an operating system for executing a software application and controlling access to said memory bus by said first and second processors so that management of said memory bus is transparent to said software application operating on said control system thereby permitting said first and second processors to appear to act as a single logical processor to said software application.

7. The control system for said dialysis machine of claim 6, further comprising:

a bus bridge coupled to said memory bus;

an I/O bus coupled to said bus bridge;

a plurality of I/O devices coupled to said I/O bus; and a plurality of sensors coupled to said I/O bus.

8. The control system for a dialysis machine of claim 7 wherein the plurality of I/O devices comprises active hardware components for said dialysis machine.

9. The control system for a dialysis machine of claim 4 wherein said operating system manages access to said memory bus for said plurality of processors by distributing a set of processor instructions between said plurality of processors.

10. The control system for the dialysis machine of claim 9 wherein said operating system manages access to said memory bus via said plurality of processors by distributing a set of processor instructions from a process to said plurality of processors.

11. The control system for the dialysis machine of claim 9 wherein said operating system manages a plurality of processes and access to said memory bus via said plurality of processors by distributing a set of processor instructions from said plurality of processes to said plurality of processors.

12. The control system for the dialysis machine of claim 9, wherein the plurality of processors comprises a first and a second processor and wherein the plurality of caches comprises a first cache coupled with the first processor and a second cache coupled to the second processor.

13. The control system of claim 7, wherein the control system for the dialysis machine further comprises:

an SMP processor board wherein the first and second processors and the first and second caches are resident on said SMP processor board;

said at least one adapter board having circuitry receiving input signals from the plurality of sensors and passing the input signals to the I/O bus;

at least one motor and valve driver board sending commands to the plurality of I/O devices from the I/O bus;

a plurality of hardware watchdogs coupled to the I/O bus, said plurality of hardware watchdogs incorporated into one or more of said at least one adapter boards; and said hardware watchdogs providing a reset signal to said SMP processor board, said at least one adapter board and said at least one driver board in response to a failure of the first and second processor to reset the watchdog timer thereby placing said dialysis machine in a patient safe condition.

14. A method for operating a dialysis machine, comprising the steps of:

executing a plurality of software processes on a plurality of processors sharing a common main memory, wherein said plurality of processors appear to act as a single logical processor to a software application for said dialysis machine;

resetting a plurality of hardware watchdog timers by said plurality of processors before said hardware watchdog timers time out, and if said plurality of processors fails to reset said plurality of watchdog timers and if at least one of said plurality of watchdog timers time-out, then at least one of said plurality of hardware watchdog timers reset at least one of said plurality of processors.

15. The method of operating a dialysis machine in claim 14, wherein said dialysis machine is placed in a patient-safe state if said plurality of processors fail to reset the watchdog timers.

16. The method of operating a dialysis machine in claim 15, wherein said plurality of processors appearing to act as a single logical processor to a software application for said dialysis machine, and wherein said method further comprises the steps of:

controlling access to a memory bus coupled to the plurality of processors by an operating system;

wherein said access controlled by said operating system is performed by scheduling instructions to be executed on said plurality of processors thereby permitting said operating system to manage the plurality of processors in a manner that is transparent to said software application.

17. The method of operating a dialysis machine in claim 16 wherein said operating system distributes a plurality of instructions from a plurality of software processes to the plurality of processors.

18. The method of operating a dialysis machine in claim 17 wherein said operating system distributes said plurality of instructions from any one of said plurality of processes to the plurality of processors.

19. The method of operating a dialysis machine in claim 17 wherein said operating system distributes said plurality of instructions from said plurality of processes to the plurality of processors such that each of the plurality of processors works on a different process from the plurality of processes.

20. The method of operating a dialysis machine in claim 17, further comprising the step of:

updating a plurality of caches coupled to one of each of said plurality of processors and a memory bus when said main memory is accessed; and accessing said plurality of caches associated by one of each of the plurality of processors.

21. A control system for a dialysis machine, the control system comprising:

an I/O bus;

a processor board coupled to the I/O bus having a plurality of processors and a main memory shared by said plurality of processors forming a symmetrical, multi-processing computing platform;

a plurality of host analog and adapter boards coupled to the I/O bus wherein each host analog and adapter board has a hardware watchdog timer coupled to the plurality of processors such that the plurality of hardware watchdog timers reset at least one of said plurality of processors in the event of a failure of said at least one of said processors; and a driver board coupled to the I/O bus wherein the driver board is coupled to a plurality of extracorporeal devices.

22. The control system for said dialysis machine of claim 21 wherein the plurality of host analog and adapter boards are coupled to a plurality of passive sensors and the driver board sends signals to the plurality of extracorporeal devices.

23. The control system for said dialysis machine of claim 21 wherein the extracorporeal devices are selected from the group consisting of: blood pumps, motors, heaters, and valves.

24. The control system for said dialysis machine of claim 21 wherein there are two processors and two hardware watchdog timers.

* * * * *